US008870861B2

(12) United States Patent
El-Galley et al.

(10) Patent No.: US 8,870,861 B2
(45) Date of Patent: *Oct. 28, 2014

(54) ELECTROSURGICAL CONTROL SYSTEM

(75) Inventors: Rizk El-Galley, Birmingham, AL (US); David Austin Alexander, Sterrett, AL (US); Mary Hawn, Birmingham, AL (US)

(73) Assignee: Stryker Corporation, Kalamazoo, MI (US)

( * ) Notice: Subject to any disclaimer, the term of this patent is extended or adjusted under 35 U.S.C. 154(b) by 1784 days.

This patent is subject to a terminal disclaimer.

(21) Appl. No.: 11/696,034

(22) Filed: Apr. 3, 2007

(65) Prior Publication Data

US 2007/0185480 A1  Aug. 9, 2007

Related U.S. Application Data

(63) Continuation of application No. 10/978,218, filed on Oct. 28, 2004, now Pat. No. 7,217,269.

(60) Provisional application No. 60/514,990, filed on Oct. 28, 2003.

(51) Int. Cl.
*A61B 18/14* (2006.01)
*A61B 18/00* (2006.01)
*A61B 17/00* (2006.01)
*A61B 18/04* (2006.01)
*A61B 18/12* (2006.01)

(52) U.S. Cl.
CPC ... *A61B 18/1402* (2013.01); *A61B 2018/00988* (2013.01); *A61B 2017/00225* (2013.01); *A61B 2017/00199* (2013.01); *A61B 18/042* (2013.01); *A61B 2018/124* (2013.01); *A61B 2218/008* (2013.01)
USPC .............................................. 606/34; 606/41

(58) Field of Classification Search
CPC .... A61B 18/14; A61B 18/1206; A61B 18/18; A61B 18/1492; A61B 2018/00178; A61B 2018/00875; A61B 2018/00654; A61B 2018/00988; A61B 2018/00791
USPC ............ 606/1, 10, 34, 46; 600/101, 104, 105, 600/113, 131
See application file for complete search history.

(56) References Cited

U.S. PATENT DOCUMENTS 5,288,544 A   2/1994   Mallen et al.
5,336,218 A   8/1994   Linhares
(Continued)

FOREIGN PATENT DOCUMENTS

CA    2 259 272    12/1997
CA    2 353 016    1/2002
(Continued)

OTHER PUBLICATIONS

International Search Report for International Application No. PCT/US2009/034425 (mailed Sep. 24, 2009).

(Continued)

*Primary Examiner* — Michael Peffley
(74) *Attorney, Agent, or Firm* — Flynn, Thiel, Boutell & Tanis, P.C.

(57) ABSTRACT

An electrosurgical control system includes a selector by which a user can select any of a number of electrosurgical devices or similar devices for use, and a processor system responsive to user actuation of a foot control or other central control by controlling the selected device. Each device has an associated intelligent adapter that communicates information relating to device with which the adapter is associated. The processor system uses the information communicated by the adapter to properly interface the associated device with the control system and its central control.

20 Claims, 15 Drawing Sheets

(56) References Cited

U.S. PATENT DOCUMENTS

| | | | |
|---|---|---|---|
| 5,400,267 A | 3/1995 | Denen et al. | |
| 5,540,683 A * | 7/1996 | Ichikawa et al. | 606/40 |
| 5,613,966 A | 3/1997 | Makower et al. | |
| 5,732,712 A | 3/1998 | Adair | |
| 5,788,688 A | 8/1998 | Bauer et al. | |
| 5,910,139 A | 6/1999 | Cochran et al. | |
| 6,017,354 A | 1/2000 | Culp et al. | |
| 6,055,458 A | 4/2000 | Cochran et al. | |
| 6,165,169 A * | 12/2000 | Panescu et al. | 606/1 |
| 6,612,310 B2 | 9/2003 | Sklar | |
| 6,652,514 B2 | 11/2003 | Ellman et al. | 606/37 |
| 6,666,860 B1 * | 12/2003 | Takahashi | 606/34 |
| 6,824,539 B2 | 11/2004 | Novak | |
| 6,899,538 B2 * | 5/2005 | Matoba | 433/114 |
| 6,911,916 B1 | 6/2005 | Wang et al. | |
| 7,217,269 B2 | 5/2007 | El-Galley et al. | 606/34 |
| 7,883,458 B2 | 2/2011 | Hamel | |
| 2001/0029315 A1 * | 10/2001 | Sakurai et al. | 600/101 |
| 2002/0156466 A1 | 10/2002 | Sakurai et al. | |
| 2005/0143724 A1 | 6/2005 | El-Galley et al. | |
| 2006/0184164 A1 | 8/2006 | Malis et al. | 606/34 |
| 2008/0140158 A1 | 6/2008 | Hamel et al. | |

FOREIGN PATENT DOCUMENTS

| | | |
|---|---|---|
| JP | 2002-306504 | 10/2002 |
| WO | WO 97/49340 | 12/1997 |

OTHER PUBLICATIONS

Written Opinion of the International Searching Authority for International Application No. PCT/US2009/034425 (mailed Sep. 24, 2009).

* cited by examiner

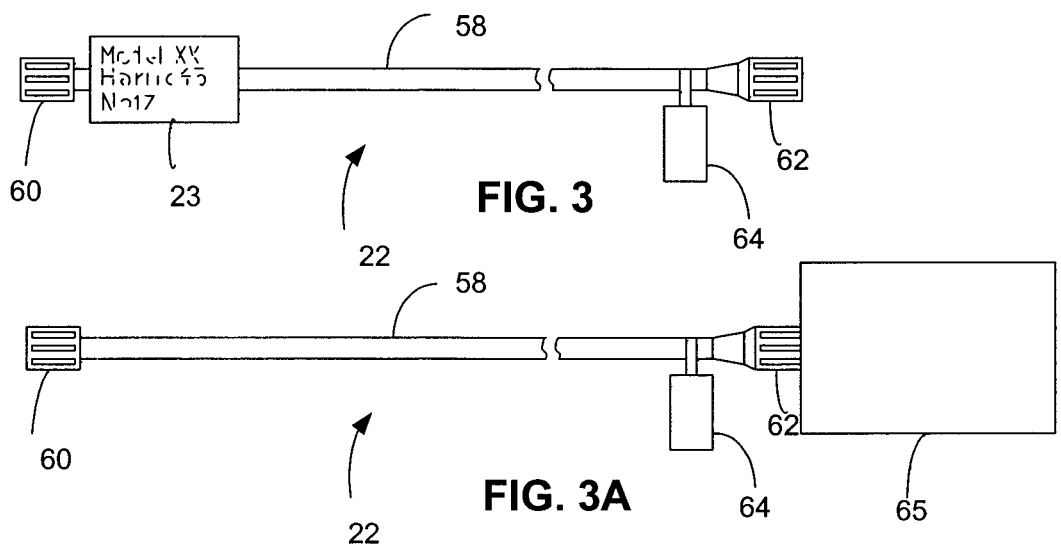
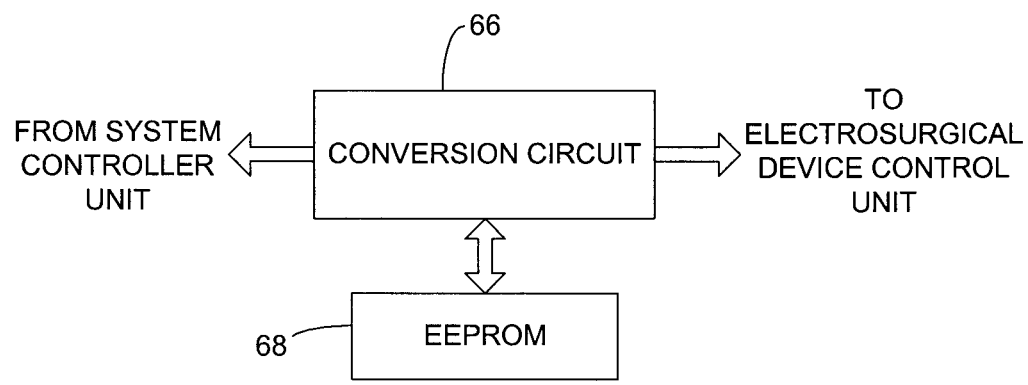

ELECTROSURGICAL CONTROL SYSTEM

CROSS-REFERENCE TO RELATED APPLICATIONS

This application is a continuation application of U.S. application Ser. No. 10/978,218, filed on Oct. 28, 2004, now U.S. Pat. No. 7,217,269, which claims priority to U.S. Provisional Application No. 60/514,990 filed on Oct. 28, 2003, all of which are incorporated herein in their entirety.

BACKGROUND OF THE INVENTION

1. Field of the Invention

The present invention relates generally to electrosurgical devices and, more specifically, to controlling multiple electrosurgical devices from a single controller.

2. Description of the Related Art

Laparoscopic surgery is increasingly common. The principle of laparoscopic surgery is to perform a surgical procedure with small keyhole incisions. Usually, two or three such keyhole incisions are made in the abdomen for insertion of a telescopic video camera, laparoscopic instruments and electrosurgical devices. Electrosurgical devices are used in both open surgical and laparoscopic surgical procedures to cut and coagulate tissue. Various types of electrosurgical devices are known, including those that use diathermy with either unipolar or bipolar current, and advanced devices such as harmonic scissors and argon beam and laser devices. Monopolar and bipolar devices use one or two electrodes, respectively, to deliver electrical energy from a current source to the surgical site. By varying the voltage, current, or waveform of the electrical energy delivered by the electrode, surgeons can cut tissue cleanly, coagulate tissue to stop bleeding, or produce a "blended cut" that combines these two functions.

A surgeon may use more than one electrosurgical device in a major surgical procedure. The surgeon operates each device independently of the others, typically using a foot pedal control connected to the device. Thus, the surgeon may have at his or her feet several foot pedal controls, each for operating a different device. Multiple foot pedal controls on the floor beneath the operating table create the potential for confusion and increased risk of injury when the surgeon looks under the table to locate the foot pedal control associated with the particular electrosurgical device he or she intends to use, thereby losing sight of the surgical field. The potential for confusion is compounded by the foot pedals of different devices having different uses or functions. For example, unipolar electrosurgical devices commonly have two foot pedals: depressing one pedal causes the device to apply a high-power signal to the electrode for cutting tissue; depressing the other pedal causes the device to apply a lower-power signal to the electrode for coagulating tissue. Bipolar electrosurgical devices most commonly have only one foot pedal, which, when depressed, causes the device to energize or apply a signal to the electrode, i.e., it turns the power on. (Releasing it de-energizes the electrode.) Some bipolar devices include a second pedal, but the functions of the two pedals of a bipolar device are different from those of unipolar devices: depressing one pedal causes the bipolar device to, as described above, turn the power on; depressing the other pedal causes the device to increase the power (proportionately to the amount of time that pedal is depressed). Thus, there is a rist of injury due to surgeon confusion arising from the differing functions associated with the foot pedals.

Additionally, because the surgeon may operate multiple electrosurgical devices independantly from each other in a major surgical proceudre, there is no system to evacuate smoke when the devices perform cutting or coagulation functions. Delay evactuating smoke can cause difficulty in viewing the surgical field and may neccessiate delay in the surgery while smoke is evactuated from the surgical field. Further, in the past, sugeons would have to stop using one electrosurgical device to insert a vacuum and remove any smoke and debris, causing further delay in the surgical procedure.

It would be desirable to provide a control system for electrosurgical devices operated by foot pedals or similar controls that alleviates the potential for confusion and that allows for activation of a smoke evacuation system when a surgical function is performed. The present invention addresses this problem and others in the manner described below.

SUMMARY OF THE INVENTION

The present invention relates to a control system that allows a surgeon or other user to use a central control, such as a foot control, to operate a plurality of independent electrosurgical devices, each of which would otherwise need to be individually controlled by an associated foot control or other device control.

The control system includes a device selector by which a user can select an instrument for use. The control system also includes a processor system that is programmed or adapted to respond to user actuation of the central control by controlling the selected electrosurgical device. Because each device may have input requirements or other interface considerations that are different from those of the other devices of the plurality, an intelligent adapter is provided for each device. Each adapter is programmed or adapted to communicate information relating to the device with which it is associated. The processor system uses the information communicated by the adapter to properly interface the associated device with the control system and its central control. Thus, for example, in exemplary embodiments of the invention, a surgeon can use a central foot control to control any selected one of a number of electrosurgical devices connected to the control system that would otherwise need to be controlled by a corresponding number of individual foot controls.

It is to be understood that both the foregoing general description and the following detailed description are exemplary and explanatory only and are not restrictive of the invention, as claimed.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein:

FIG. 3 illustrates an intelligent adapter of the system;

FIG. 3A illustrates an intelligent adapter of the system for a "smart" electrosurgical device.

FIG. 4 is a block diagram of the intelligent adapter;

DETAILED DESCRIPTION

Figure 1:
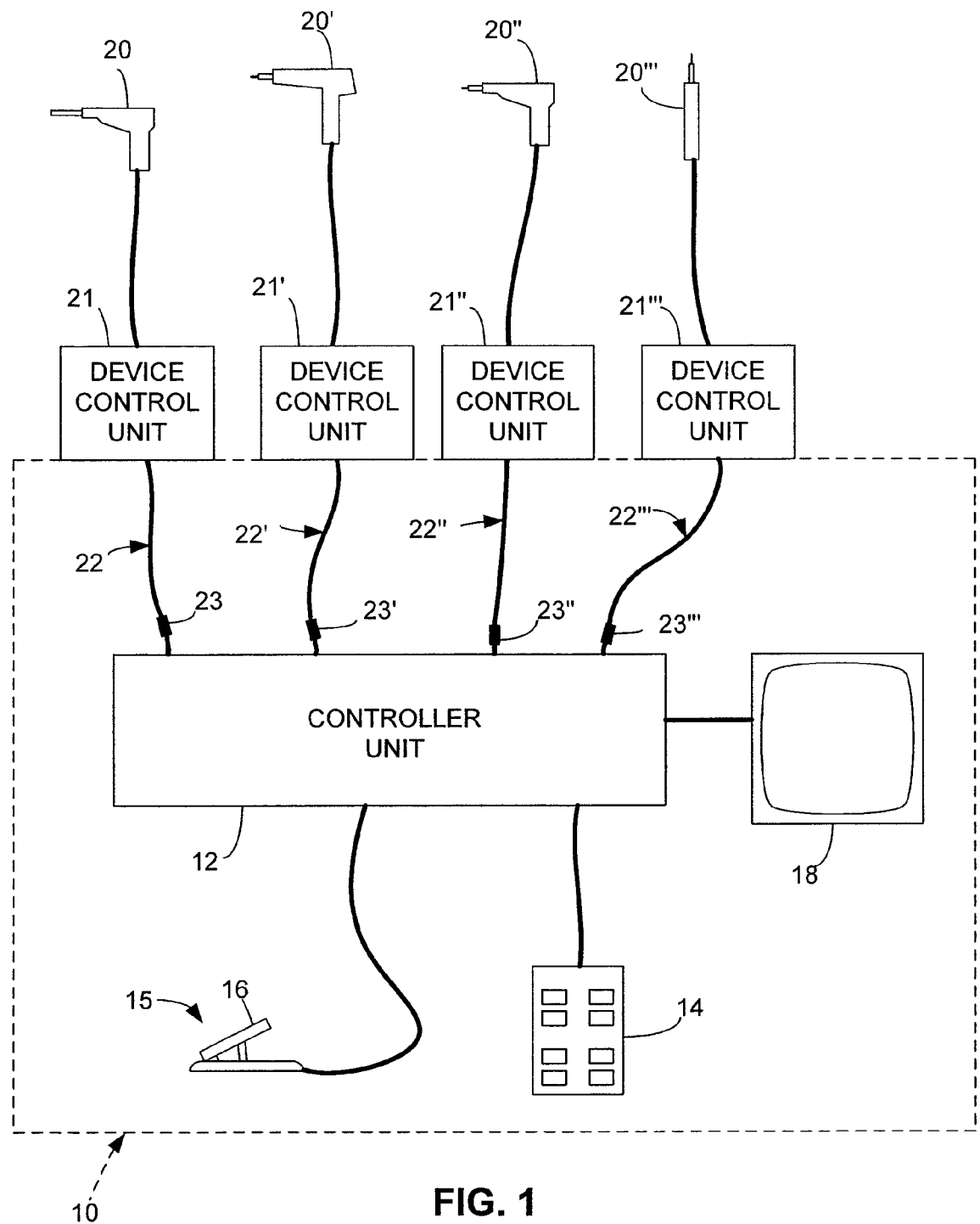
FIG. 1 illustrates a control system for electrosurgical and other devices in accordance with one embodiment of the invention.

As illustrated in FIG. 1, an electrosurgical control system 10 includes a central controller unit 12, a device selector such as a remote controller 14, a central user control 15 such as a foot control 16, and a display 18 that can be either a dedicated display or monitor for the purposes described below or, in some embodiments of the invention, can be the monitor that displays laparoscopic video imagery for a surgeon. System 10 is shown in FIG. 1 as, for exemplary purposes, controlling four electrosurgical tools or instruments 20, 20', 20" and 20'" via their associated device control units 21, 21', 21" and 21''', but in other embodiments can control any suitable number and type of such instruments. Each of instruments 20, 20', 20" and 20''' is controlled by and communicates with control system 10 via a channel. Thus, in the illustrated embodiment, control system 10 has a first, second, third and fourth channel, but in other embodiments can have more or fewer channels.

The term "device" or "electrosurgical device" is used in this patent specification to refer to not just the instrument (e.g., 20, 20', 20" and 20''') itself, but rather, if the instrument is usable in combination with a control unit (e.g., 21, 21', 21" and 21''') that may be conventionally associated with the instrument, to the combination of the instrument and its associated control unit. In other words, an "electrosurgical device" comprises the electrosurgical instrument (e.g., 20, 20', 20" and 20''') and its device control unit (e.g., 21, 21', 21" and 21''', respectively) that are conventionally intended to be used together or sold together commercially as a unitary product. Thus, it is the instrument and its associated control unit that are well-known in the art and commercially available but with which the novel control system 10 of the present invention can be used in combination as described in this patent specification. In addition, when an electrosurgical device is obtained commercially, although not shown in FIG. 1 for purposes of clarity, an associated foot control (much like foot control 16) or other device user control can be connected directly to the associated device control unit. As known in the art, by depressing the pedals of such a device user control, the surgeon or other user can operate the associated one of electrosurgical instruments 20, 20', 20" and 20''' in the manner known in the art.

Electrosurgical instruments 20, 20', 20" and 20''' and others like them can be of any suitable type known in the art, including those that use diathermy with either unipolar or bipolar current (commonly referred to simply as unipolar devices and bipolar devices), and advanced devices such as harmonic scissors and argon beam and laser devices. The illustrated shapes and other structural features of instruments 20, 20', 20" and 20''' as depicted in FIG. 1 are not intended to describe the instruments specifically but rather are intended only to convey the general concept that various instruments can be used. Indeed, it is important to note that the present invention facilitates the integration of instruments that may have different functions and other characteristics in terms of how they respond to their associated device user controls (not shown) and in terms of the signals produced by their device user controls that characterize their operation. For example, instruments 20, 20' and 20" can have functions that differ from those of each other as a result of instrument 20 being, for example, a unipolar device, while instrument 20' is, for example, a bipolar device, and instrument 20" is a harmonic device. In addition, it may be that, for example, instruments 20 and 20' have different operating characteristics from each other because they require signals of different voltages from each other. The various devices may be produced by different manufacturers or be different versions or models of a device. Regardless of any such differences, control system 10 ensures that any and all of the instruments to which it is connected can be controlled by foot control 16 or other central user control.

Control system 10 further includes intelligent adapters 22, 22', 22", and 22''', each associated with one of instruments 20, 20', 20" and 20''', respectively. Each of intelligent adapters 22, 22', 22" and 22''' includes a suitable cable and may include an adapter module 23, 23', 23" and 23''', respectively, which comprises an enclosure for the intelligent electronics described below that are programmed or adapted to interface foot control 16 with a user-selected one of instruments 20, 20', 20" and 20''' as described in further detail below. The intelligent adapters 22, 22', 22", and 22''' include an adapter module 23, 23', 23" and 23''' when the instrument 20, 20', 20" and 20''' is a "dumb" instrument, i.e. one that has no computer communication port. When the instrument is a "smart" instrument i.e. one that has a computer communication port and intelligent electronics, then the intelligent adapter 22, 22', 22", and 22''' may include only a cable. Thus, for example, although absent control system 10, a surgeon would have to use four separate foot controls (not shown), each associated with one of instruments 20, 20', 20" and 20''', by using the novel control system 10 of the present invention, the surgeon can select any one of instruments 20, 20', 20" and 20''' and use foot control 16 to control it. By making such selections from time to time as needed during a surgery, the surgeon can readily use any or all of instruments 20, 20', 20" and 20''' without moving from foot control 16 and without diverting his or her eyes from the surgical field.

Figure 2:
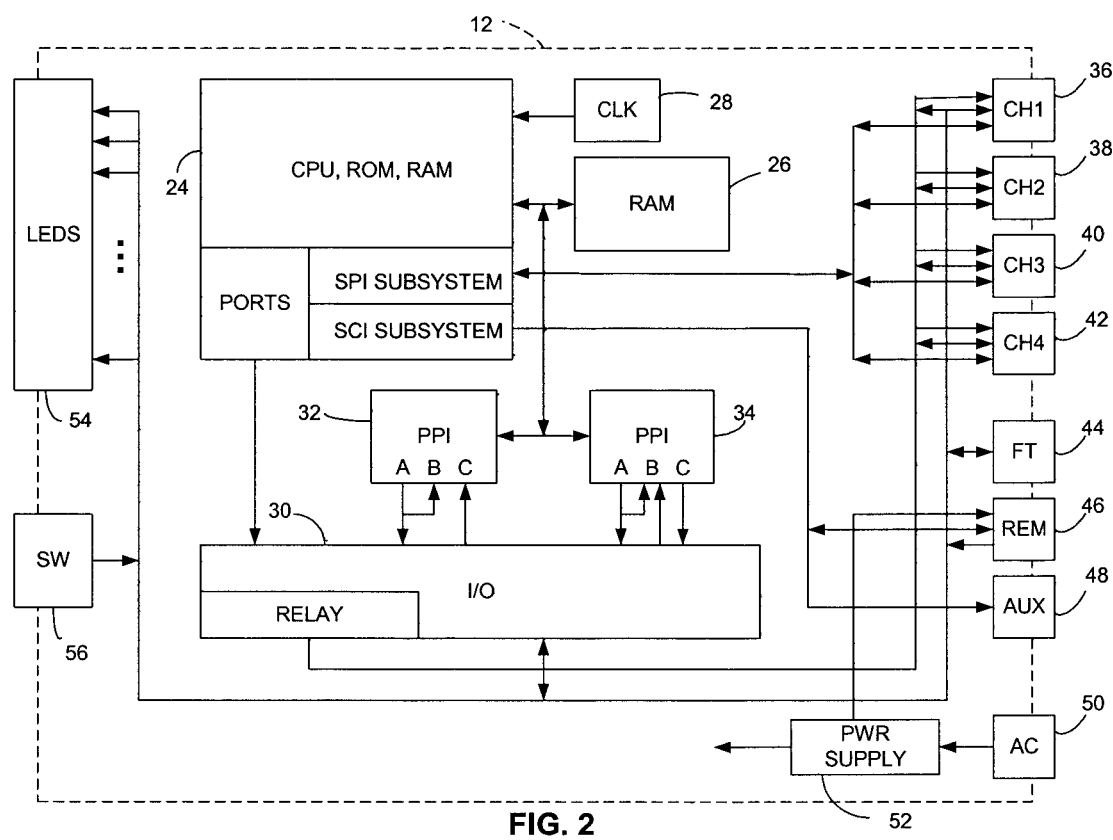
FIG. 2 is a block diagram of a controller unit of the system.

As illustrated in FIG. 2, in an exemplary embodiment of the invention, central controller unit 12 includes, within a suitable electronics enclosure or housing (not shown), a processor system having a microcontroller 24 with a central processing unit (CPU) that is programmed to effect the method steps described below. The programming can be stored in suitable read-only memory (ROM). Suitable random-access memory (RAM) 26 is also included to enable proper operation of the CPU. These memories can be integrally formed in microcontroller 24 along with the CPU and other portions generally included in microcontrollers and microprocessors or can be external to it in other embodiments. The MC68HC711E20, available from Motorola, is an example of a suitable microcontroller 24. A system clock 28 is also included to enable proper operation of microcontroller 24. In view of the description below of the method steps, persons skilled in the art will be capable of providing suitable programming and otherwise configuring and using central controller unit 12.

Ports of microcontroller 24 are coupled to input/output (I/O) circuitry 30, as are two programmable peripheral interfaces (PPIs) 32 and 34. The 82C55, available from OKI Semiconductor, is an example of a suitable PPI. Input/output circuitry 30 interfaces the above-described logic with channel connectors 36, 38, 40 and 42, a foot pedal connector 44, and a remote unit connector 46. Other connectors on or in the enclosure include an auxiliary data connector 48, to which a computer (not shown), a display, or other external equipment can be connected, and an AC power connector 50 through which central controller unit 12 receives power to operate its circuitry and, via remote connector 46, the circuitry of remote controller 14. A power supply circuit 52 distributes the power to such circuitry.

A computer connected to auxiliary data connector 48 can include display 18 (see FIG. 1), although such a computer is not shown in FIGS. 1 and 2 for purposes of clarity. As noted above, display 18 can be that of such a computer or can be the very laparoscopic monitor used in the surgery in which the present invention is used. As described below in further detail, a surgeon can view the monitor not only to view the laparoscopy but also to view information output by central controller unit 12. This information can be superimposed on the laparoscopic image, located in a corner of display 18 or otherwise located in a convenient position and manner on display 18. The requisite laparoscopic equipment, including its monitor or display, is well-known in the art and not illustrated in this patent specification for purposes of clarity but is present in instances in which an embodiment of the invention is used in laparoscopic surgery. Video combiner circuitry to superimpose information output by central controller unit 12 over laparoscopic imagery is not show for purposes of clarity, but suitable circuitry is well-known and commercially available.

Input/output circuitry 30 also interfaces the above-described logic with a number of suitable display elements, such as light-emitting diodes (LEDs) 54. LEDs 54 can indicate to a user, in addition to system status and error conditions, such as whether power is on, etc., whether any electrosurgical devices have been connected to connectors 36, 38, 40 and 42 and, if so, which one of them a user may have selected. Such indications are similar to those described below with regard to remote controller 14. Input/output circuitry 30 also interfaces the above-described logic with a device select switch 56 that, as described in further detail below, a user can use to select one of the connected electrosurgical devices as an alternative to using remote controller 14.

Functions of PPIs 30 and 32 are indicated below with regard to FIGS. 12 and 13A-E, which illustrate the method by which central controller unit 12 operates. The signals to which the relevant method steps relate include, as indicated in FIG. 2: signals received at port C of PPI 32 from device select switch 56; signals received at port C of PPI 32 from channel connectors 36, 38, 40 and 42 that indicate whether a device is connected; signals received at port C of PPI 32 from foot pedal connector 44 that indicate the state of each foot pedal (i.e., depressed or not depressed); signals generated at port A of PPI 32 that are provided to electrosurgical devices connected at connectors 36, 38, 40 and 42; signals received at port B of PPI 32 that read or "verify" the signal level provided to electrosurgical devices at connectors 36, 38, 40 and 42; signals generated at port C of PPI 34 that are provided to LEDs 54; signals generated at port A of PPI 34 that are provided to relay drive circuits in I/O circuitry 30 to enable signals to reach a (selected) electrosurgical device at connectors 36, 38, 40 and 42; signals received at port B of PPI 34 that read or "verify" the signal level provided to the relay drive circuits; signals received at port B of PPI 34 from connector 44 that indicate whether foot control 16 is connected; and signals received at port B of PPI 34 from connector 46 that indicate whether remote controller 14 is connected.

As illustrated in further detail in FIG. 3, each intelligent adapter (e.g., 22) includes, in addition to a suitable length of cable 58, the adapter module (e.g., 23) that houses the intelligent logic described below, and two adapter connectors 60 and 62. In preparation for use, a user can connect adapter connector 60 to any one of channel connectors 36, 38, 40 and 42, and connect adapter connector 62 to its associated device control unit (e.g., 21).

Alternatively, if a "smart" electrosurgical device 65 is used, the intelligent adapter 22 may not include an adapter module 23, as illustrated in FIG. 3A. In this embodiment, the electrosurgical device houses the intelligent logic described below.

As illustrated in FIG. 4, adapter module 23 includes an embedded microchip conversion circuit 66 (providing "intelligence" in according with its programming) and a memory 68, such as an electrically eraseable programmable read-only memory (EEPROM), from which central controller unit 12 can read information relating to the electrosurgical device associated with that intelligent adapter. Alternatively, if the electrosurgical device is "smart" the device may include an embedded microchip conversion circuit 66 and a memory 68, from which central controller unit 12 can read information relating to the electrosurgical device associated with that intelligent adapter. The information can include information identifying functions of the electrosurgical device, such as whether a foot pedal is used for activating a cutting function or a coagulation function, for turning the device on and off, or for another function. The information can include information identifying the device type, e.g., unipolar, bipolar, harmonic scissors, argon beam, etc. The information can include information identifying the manufacturer name and model number or other identifying information that may aid the user. The information can include information that characterizes the operation of the device user control (e.g., foot pedal) that is conventionally associated with the electrosurgical device. If the electrosurgical device is "smart," the information may also include information regarding the power level and adjustments thereto, unit diagnostics, and the like. Central controller unit 12 can use such information to conform the signals it provides to the electrosurgical device to the parameters under which that device conventionally operates, i.e., conventionally would receive from its associated device user control if such a device user control were connected. As indicated in FIG. 3, some of this information, such as the device type and manufacturer name and model number can be imprinted on module 23 where it can be read by a user. Similarly, such information can be imprinted on a hanging tag 64 attached to an end of the cable.

With further regard to FIG. 4, in the exemplary embodiment of the invention, conversion circuit 66 converts input control signals received from central controller unit 12 to emulate the mechanical or solid-state switch closures of a foot pedal or similar switch-based device user control. As described below in further detail, memory 68 clocks bits out serially to central controller unit 12 in response to a clock signal received from central controller unit 12.

Figure 5:
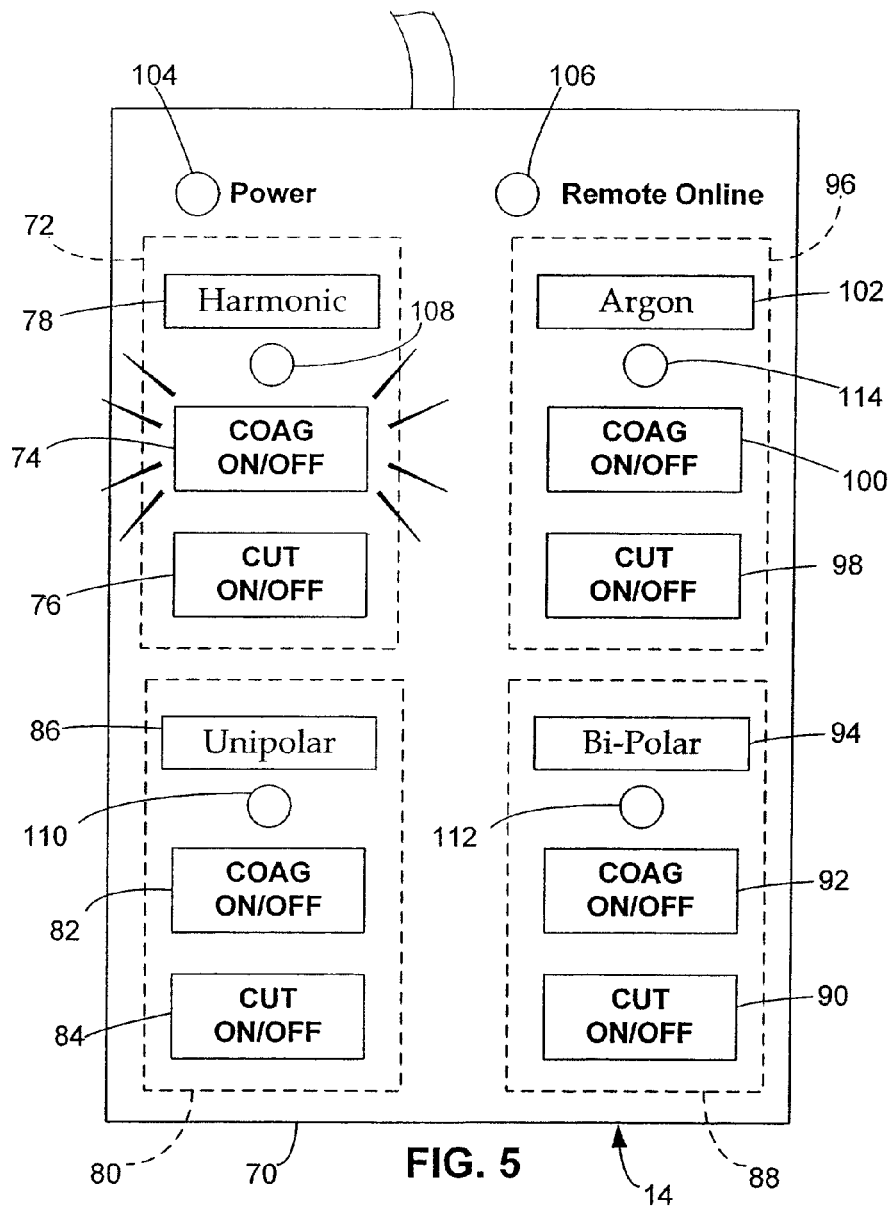
FIG. 5 illustrates a remote controller of the system for selecting devices and related functions.

As illustrated in FIG. 5, remote controller 14 functions as a device selector in a manner similar to that in which switch 56 on the operator panel of central controller unit 12 functions as a device selector. In other embodiments of the invention, a device selector can be included, alternatively or in addition, in any other convenient portion of the system. In any embodiment, the device selector is operable by a surgeon or other user to select one of the attached electrosurgical devices for use. In the illustrated embodiment, remote controller 14 includes a suitable housing or enclosure 70 connectable by a suitable length of cable to remote connector 46 (FIG. 2). Remote controller 14 can, for example, be laid on a suitable surface in the operating room and operated by a nurse in response to instructions spoken by the surgeon during the procedure. Remote controller 14 has elements defining a four-channel user interface: a first channel interface 72 with which two buttons 74 and 76 and a label 78 are associated; a second channel interface 80 with which two buttons and 82 and 84 and a label 86 are associated; a third channel interface 88 with which two buttons 90 and 92 and a label 94 are associated; and a fourth channel interface 96 with which two buttons 98 and 100 and a label 102 are associated. Remote controller 14 also includes a Power LED 104, which, when illuminated, indicates remote controller 14 is powered, and a Remote Online LED 106, which, when illuminated, indicates remote controller 14 is operational. A first channel LED 108 illuminates to indicate that a device has been plugged into channel connector 36 (FIG. 2) and is online, i.e., ready to be selected for use. A second channel LED 110 illuminates to indicate that a device has been plugged into channel connector 38 (FIG. 2) and is online. Similarly, a third channel LED 112 illuminates to indicate that a device has been plugged into channel connector 40 (FIG. 2) and is online, and a fourth channel LED 114 illuminates to indicate that a device has been plugged into channel connector 42 (FIG. 2) and is online.

Remote controller 14 can be operated to not just select one of the electrosurgical devices for use but also, at least in the illustrated embodiment of the invention, at the same time associate each input, e.g., one of the foot pedals, of foot control 16 or other central user control with one of the functions of the selected device. In FIG. 5, the four exemplary devices are: a harmonic device associated with the first channel (and thus with first channel interface 72 of remote controller 14), as indicated by the indicia "Harmonic" of label 78; a unipolar device associated with the second channel (and thus with second channel interface 80), as indicated by the indicia "Unipolar" of label 86; a bipolar device associated with the third channel (and thus with third channel interface 88), as indicated by the indicia "Bipolar" of label 94; and an argon laser device associated with the fourth channel (and thus with fourth channel interface 96), as indicated by the indicia "Argon" of label 102. In this example, the harmonic device has two functions, coagulate and cut, as indicated by the indicia on buttons 74 and 76, respectively. Similarly, the unipolar device has two functions, coagulate and cut, as indicated by the indicia on buttons 82 and 84, respectively. The bipolar device has the same two functions, as indicated by the indicia on buttons 90 and 92, as does the argon device, as indicated by the indicia on buttons 98 and 100.

By pressing the above-described buttons 74, 76, 82, 84, 90, 92, 98 and 100 a nurse or other user can associate each pedal (or other central user input) of foot control 16 (or other central user control) with one of the functions of an electrosurgical device and, by doing so, select the device for use. The button can illuminate in response to it being pressed, or there can otherwise be generated on remote controller 14 or display 18 a suitable indication that it has been pressed. For example, by pressing button 74, which in the illustrated example bears the indicia "COAG ON/OFF," the nurse or other user can associate the left pedal of foot control 16 (FIG. 1) with the coagulation function that is conventionally associated with the left pedal of the the device connected to the first channel. By pressing button 76, which in the illustrated example bears the indicia "CUT ON/OFF," the nurse or other user can associate the right pedal of foot control 16 (FIG. 1) with the cutting function that is conventionally associated with the right pedal of the device connected to the first channel. As described in further detail below, after the user has made the device selections in this manner, a surgeon depressing the left pedal of foot control 16 results in the electrosurgical device associated with the first channel applying the signals to its electrode in the conventional manner that are intended to coagulate tissue. Depressing the right pedal of foot control 16 results in that device applying the signals to its electrode that are intended to cut tissue. If the user thereafter wishes to select a different electrosurgical device, such as that associated with the third channel, the user can press button 92, which in the illustrated example bears the indicia "COAG ON/OFF," to associate the left pedal of foot control 16 (FIG. 1) with the coagulation function that is conventionally associated with the left pedal of the the device connected to the third channel. In response, button 92 illuminates and button 74 extinguishes to indicate the change. Similarly, the user can press button 90, which in the illustrated example bears the indicia "CUT ON/OFF," to associate the right pedal of foot control 16 (FIG. 1) with the cutting function that is conventionally associated with the right pedal of the the device connected to the third channel. In response, button 90 illuminates and button 76 extinguishes to indicate the change.

Note that the above-described user interface of remote controller 14 allows cross-switching. That is, a user can associate the left pedal (or other central user input) of foot control 16 (or other central user control) with one of the functions of a first electrosurgical device and associate the right pedal (or other central user input) of foot control 16 (or other central user control) with one of the functions of a second electrosurgical device. For example, it may be desired to use one of the electrical surgical devices for cutting and another one of them for coagulation. A user could, for example, press button 82, which in the illustrated example bears the indicia "COAG ON/OFF," to associate the left pedal of foot control 16 (FIG. 1) with the coagulation function that is conventionally associated with the left pedal of the device connected to the second channel, and press button 98, which in the illustrated example bears the indicia "CUT ON/OFF," to associate the right pedal of foot control 16 with the cutting function that is conventionally associated with the right pedal of the device connected to the fourth channel. As noted above, the two devices can be similar to each other or can be of different types, have different functions and be from different manufacturers.

Labels 78, 86, 94 and 102 are shown in FIG. 5 as printed on or adhered to enclosure 70, but in other embodiments of the invention (not shown) they can be dynamic, virtual labels on a display, and thus changeable automatically in response to the device type that central controller 12 detects (by reading the intelligent adapter information) has been plugged in to channel connectors 36, 38, 40 and 42 (FIG. 2). In such embodiments, buttons 74, 76, 82, 84, 90, 92, 98 and 100 can also be virtual buttons displayed on a touch-screen display integrated into remote controller 14 that are dynamically labeled in accordance with the functions that central controller 12 detects (by reading the intelligent adapter information) are associated with the two pedals or other device user inputs. Also, as noted above, in other embodiments of the invention, the devices can have functions other than cutting and coagulating, and there can be any suitable number of channels for any corresponding number of devices. Accordingly, the above-described user interface of remote controller 14 would have a corresponding number of buttons or other means for making the associations and other selections described above.

Figure 6:
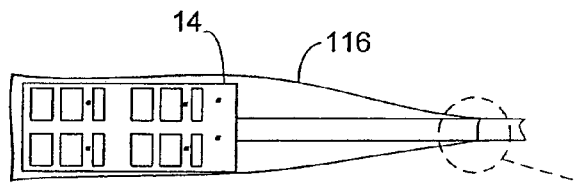
FIG. 6 illustrates the remote controller enclosed in an antistatic sheath.
Figure 7:
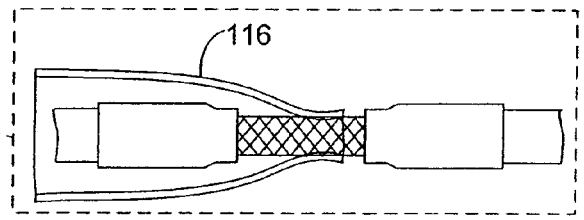
FIG. 7 is an enlargement of a portion of FIG. 6 and illustrates the sheath cinched around an electrically conductive portion of the remote controller cable for bleeding off static charge.

As illustrated in FIGS. 6 and 7, remote controller 14 and a portion of its connecting cable can be covered with a sterile, bag-like, disposable, transparent plastic sheath 116 when used (e.g., by a nurse) within the sterile field of an operating room. Sheath 116 can be made of or coated with a conductive, i.e., anti-static, material and cinched around a portion of the cable at ground potential to bleed static charge to ground, as illustrated in FIG. 7.

Figure 14:
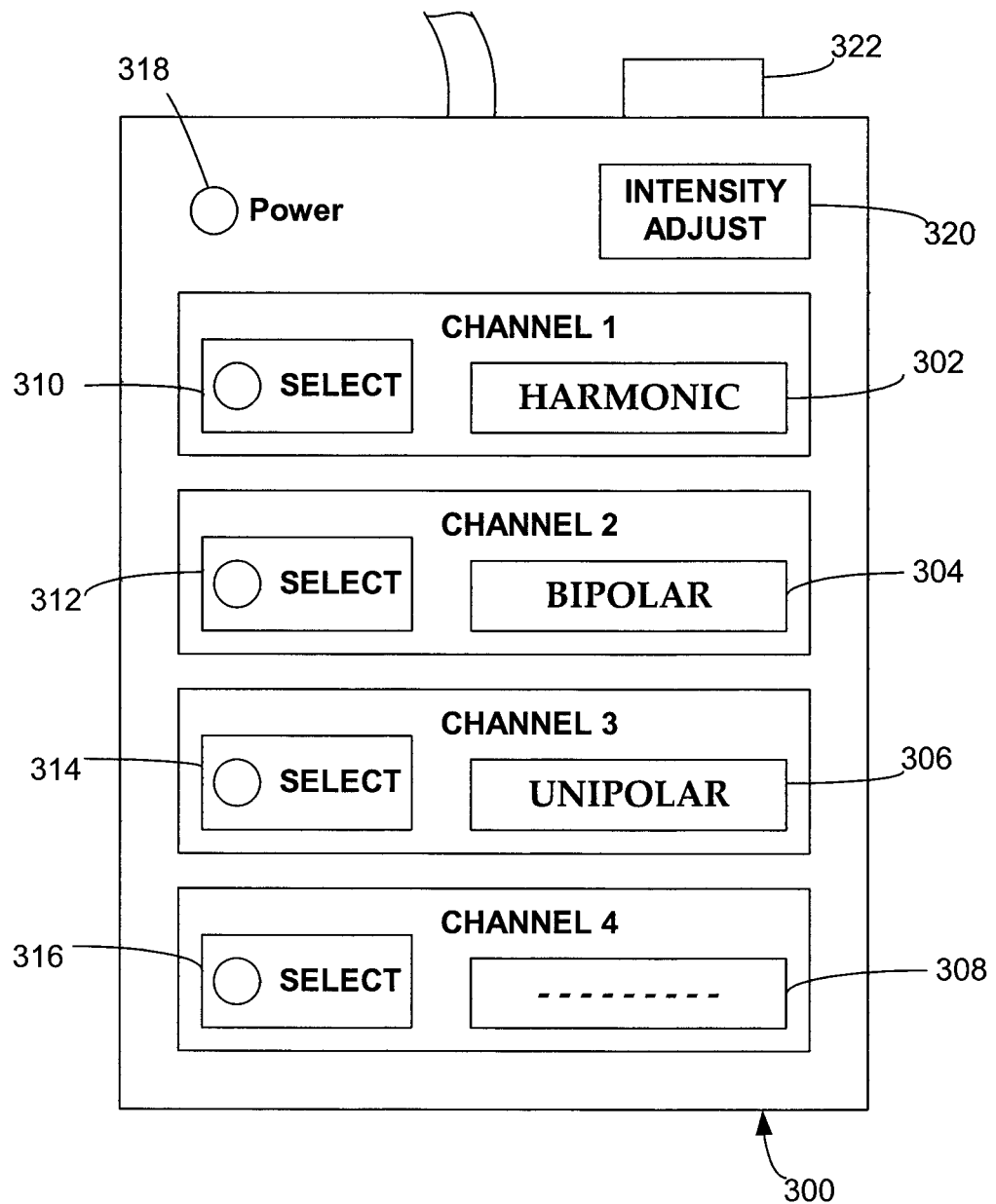
FIG. 14 illustrates an alternative remote controller.

An alternative remote controller 300 is illustrated in FIG. 14. Remote controller 300 is similar to remote controller 14, described above, but in this embodiment it does not have buttons through which an individual pedal can be associated with a device function. Rather, a user can only either select or not select each device. For example, remote controller 300 has four channels, with devices having been connected to the first, second and third channels: a harmonic device associated the first channel and its user interface, as indicated by the indicia "Harmonic" of a label 302; a bipolar device associated with the second channel and its user interface, as indicated by the indicia "Bipolar" of label 304; and a unipolar device associated with the third channel and its user interface as indicated by the indicia "Unipolar" of label 306. No device has been connected to the fourth channel, as indicated by the indicia " - - - " of label 308. As with remote controller 14, labels 302, 304, 306 and 308 can be alphanumeric displays that allow the indicia to change dynamically with the type of device that is connected. The first channel user interface has a select button 310, the second channel user interface has a select button 312, the third channel user interface has a select button 314, and the fourth channel user interface has a select button 316. Each button or an LED in the button illuminates when pressed to indicate the selection of the device connected to the corresponding channel. Remote controller 300 further includes an LED 318 to indicate the presence of power, a button 320 through which a user can adjust the intensity of the alphanumeric displays, and a button 322 through which a user can reset remote controller 300 to a default state.

Figure 8:
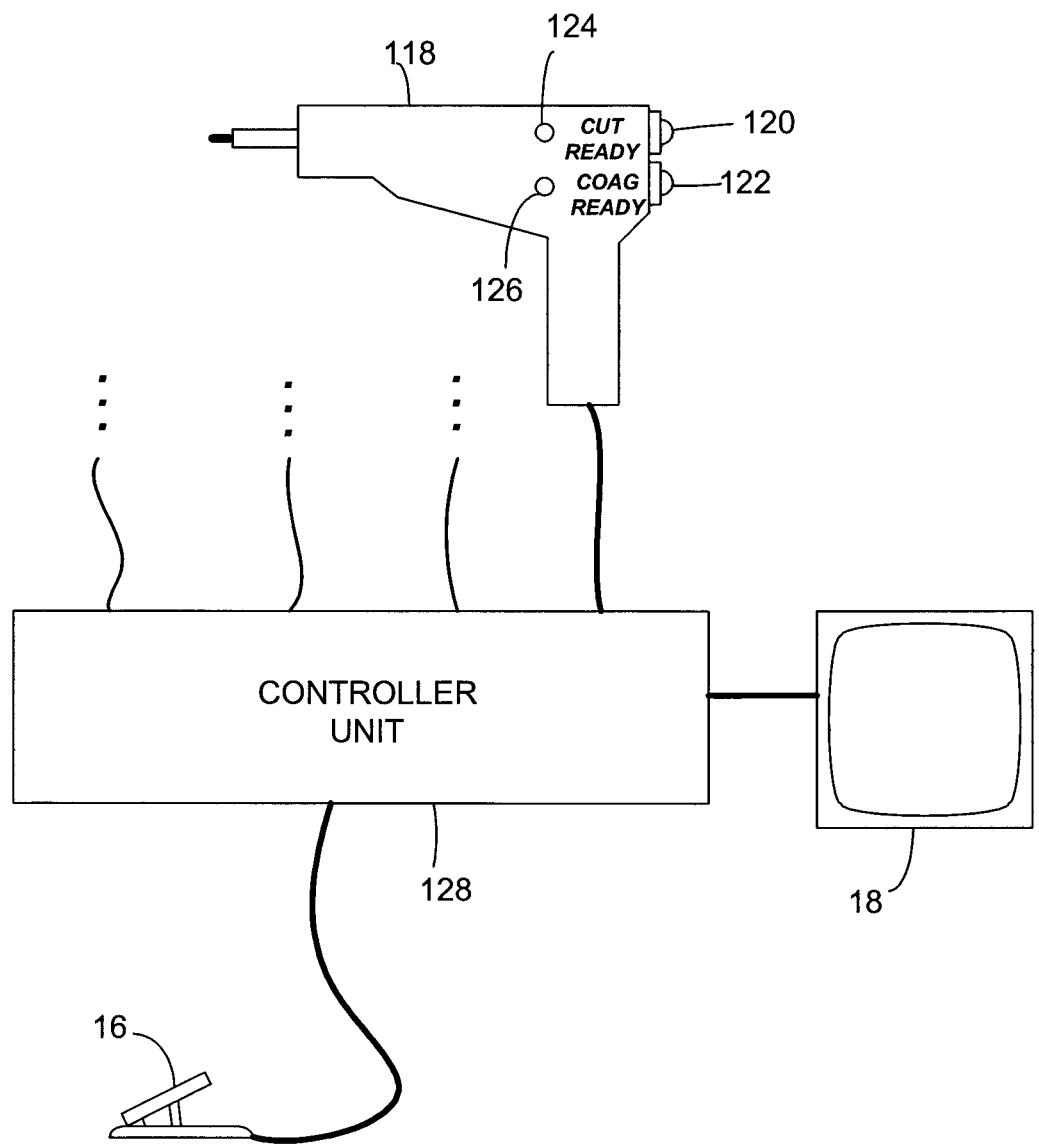
FIG. 8 is similar to FIG. 1, illustrating another embodiment of the invention in which the devices themselves have inputs for selecting them.

In another embodiment of the invention, illustrated in FIG. 8, an electrosurgical tool 118 itself can include a user interface such as switches 120 and 122 and LEDs 124 and 126, through which a user can select the device for use and associate the pedals of foot control 16 with the functions of tool 118. For example, by pressing switch 120, the user can select and associate the cutting function with the left foot pedal, and by pressing switch 122 the user can select and associate the coagulation function with the right foot pedal. LEDs 124 and 126 illuminate to indicate these selections. Alternatively, in other embodiments, tool 118 can have only one switch, which is used to enable operation of the tool in response to foot control 16. Alternatively, in still other embodiments, switches 120 and 122 can be used instead of foot control 16 to operate tool 118. The central controller unit 128 of such embodiments otherwise is constructed and operates in a manner similar to that described above with regard to FIGS. 1 and 2.

Figure 9:
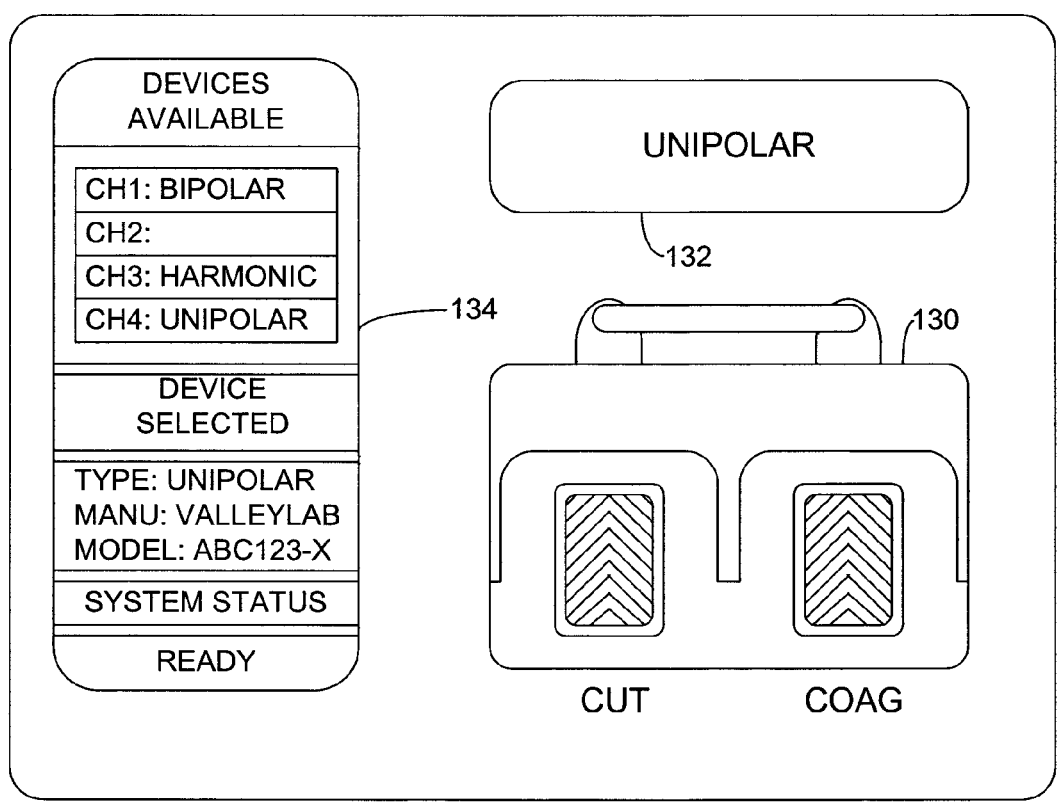
FIG. 9 illustrates an exemplary screen display produced by the system.
Figure 10:
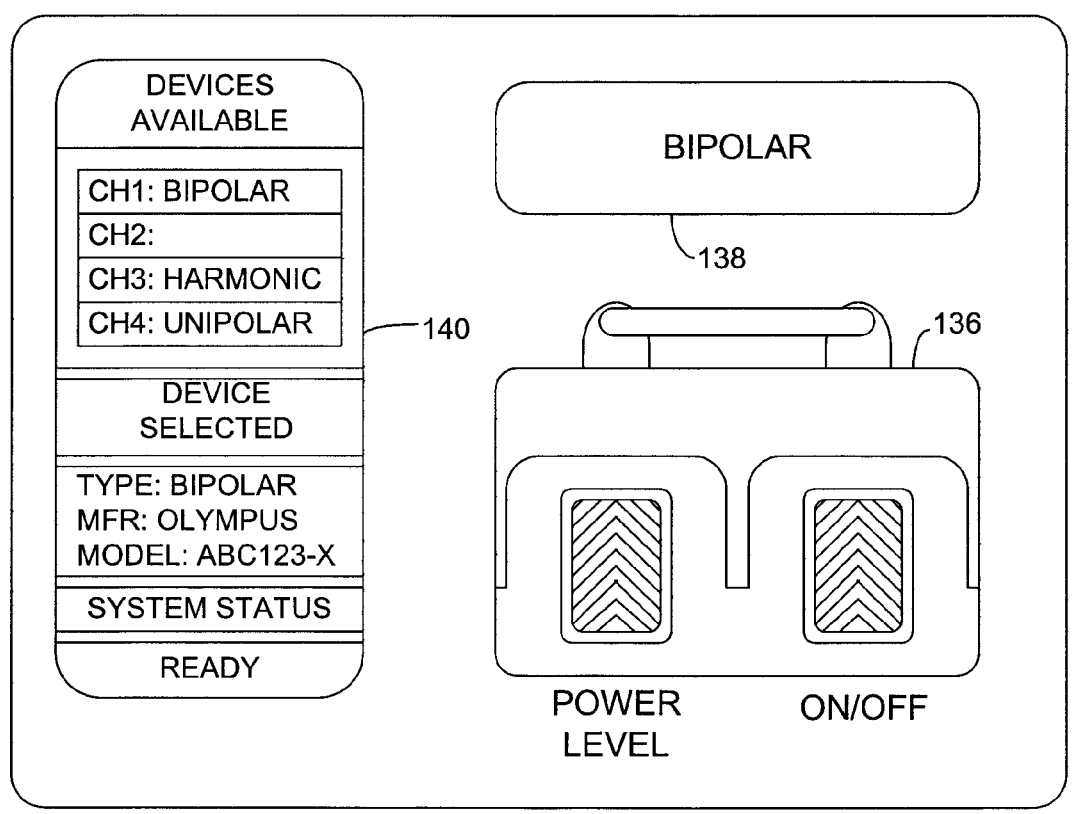
FIG. 10 illustrates another exemplary screen display produced by the system.
Figure 11:
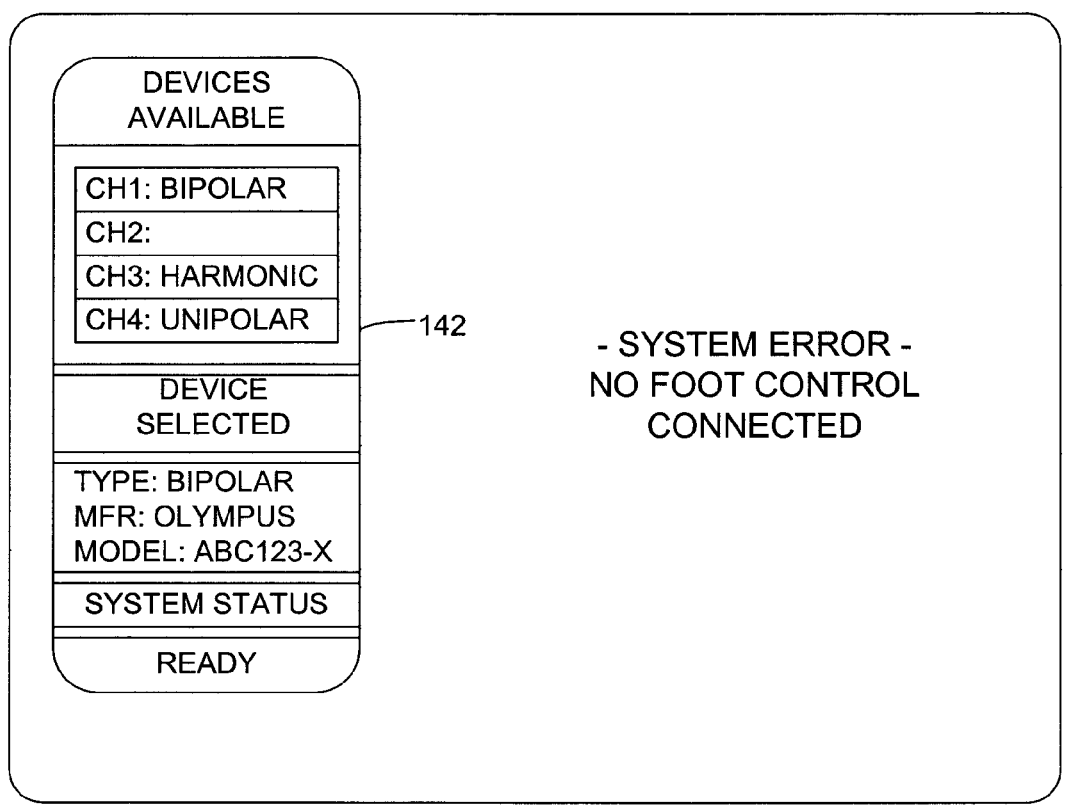
FIG. 11 illustrates a further exemplary screen display produced by the system.
Figure 12:
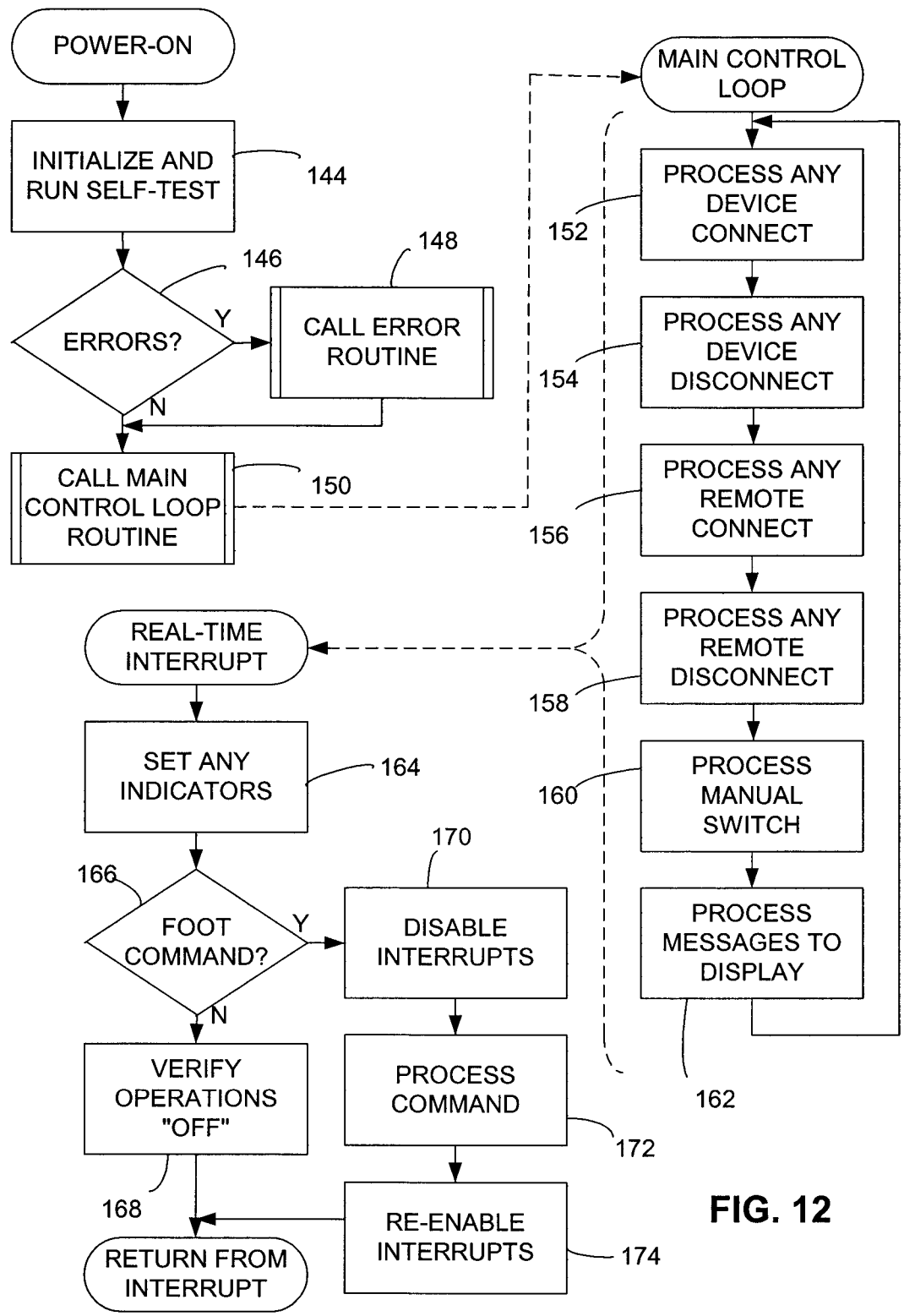
FIG. 12 is a flow diagram illustrating a method by which the illustrated embodiment of the system operates.
Figure 13A:
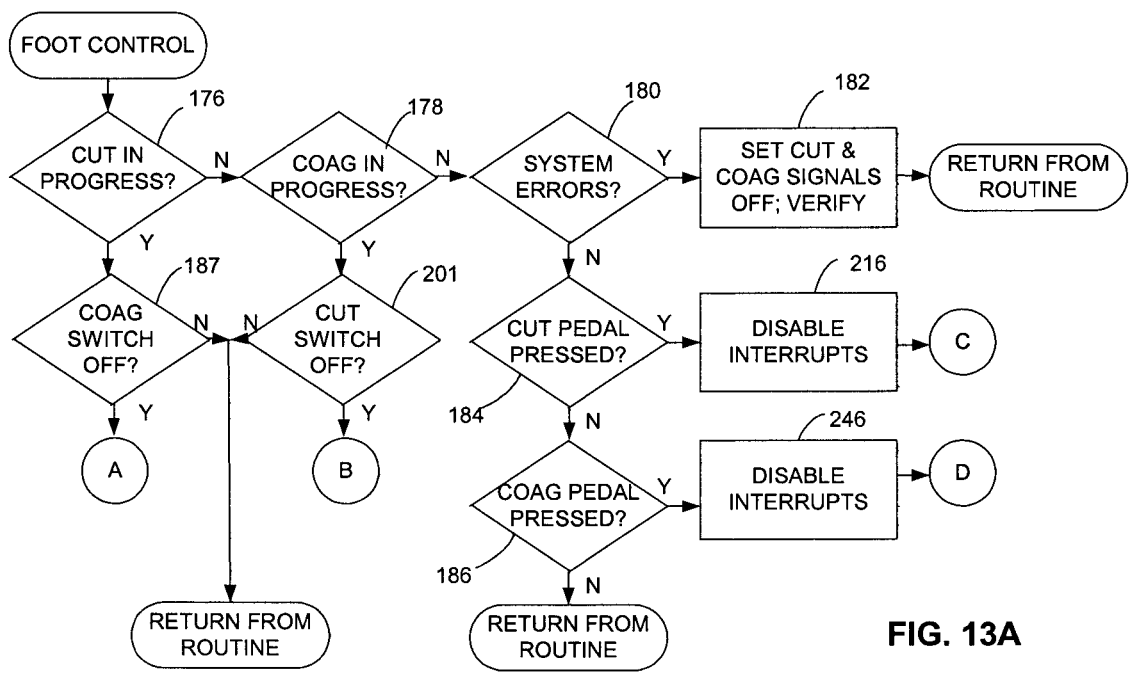
FIG. 13A is a flow diagram illustrating a portion of the method.
Figure 13B:
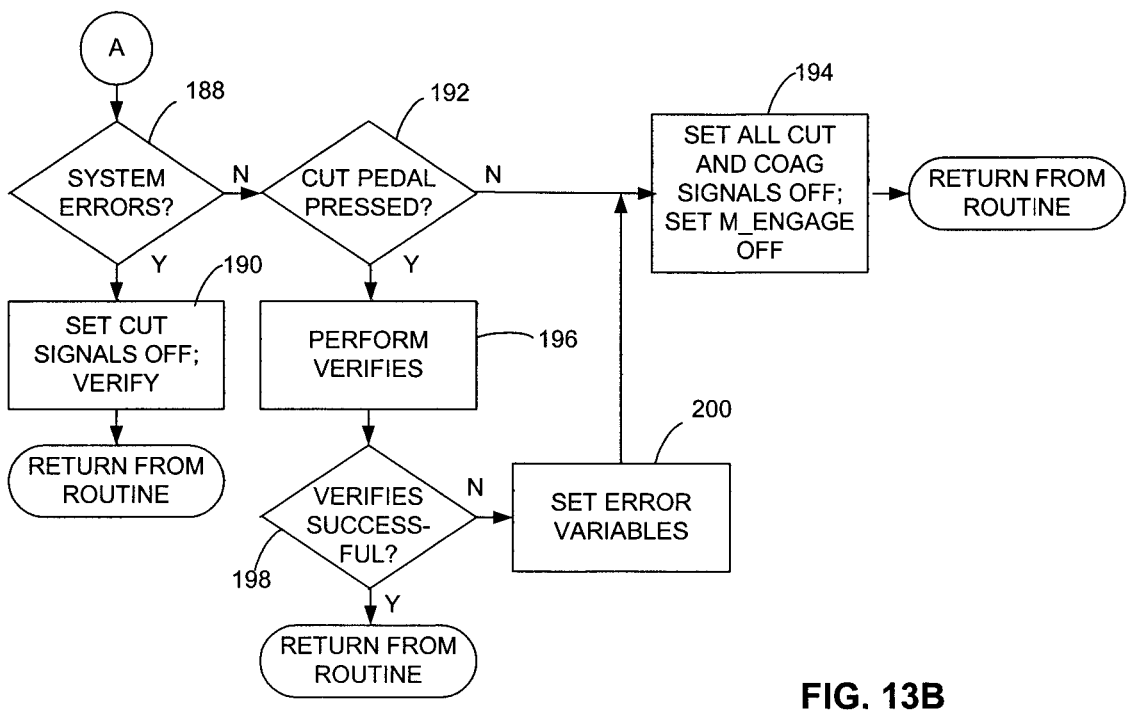
FIG. 13B is a continuation of the flow diagram of FIG. 13A.
Figure 13C:
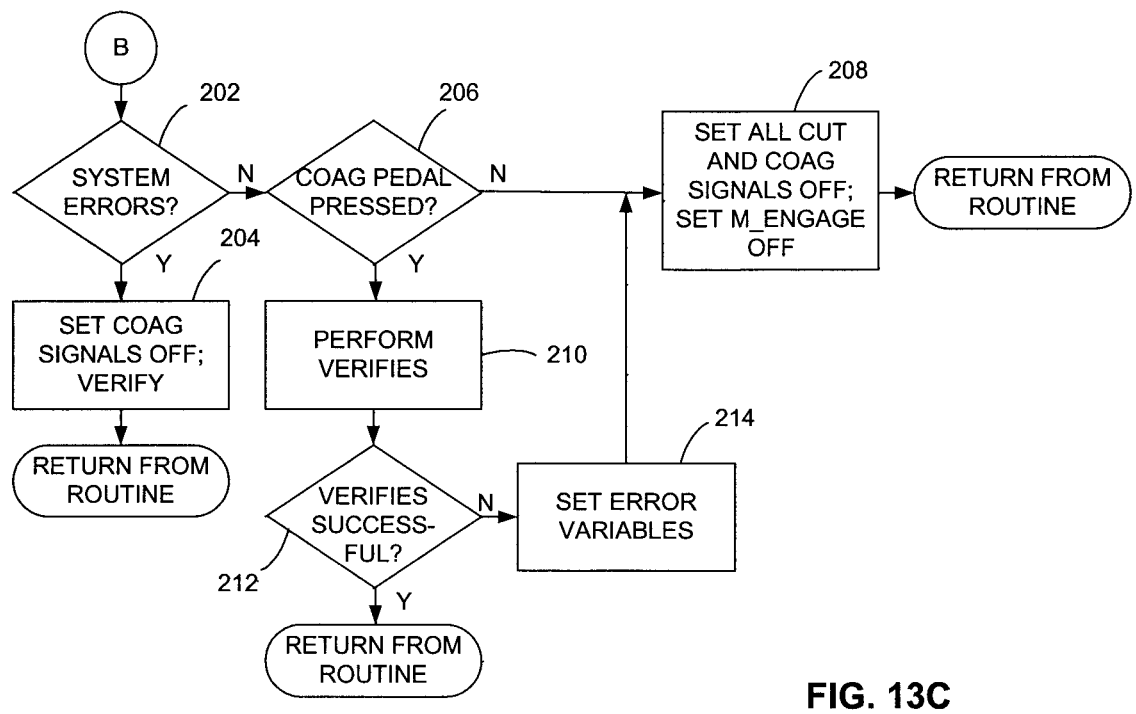
FIG. 13C is a continuation of the flow diagram of FIGS. 13A-B.
Figure 13D:
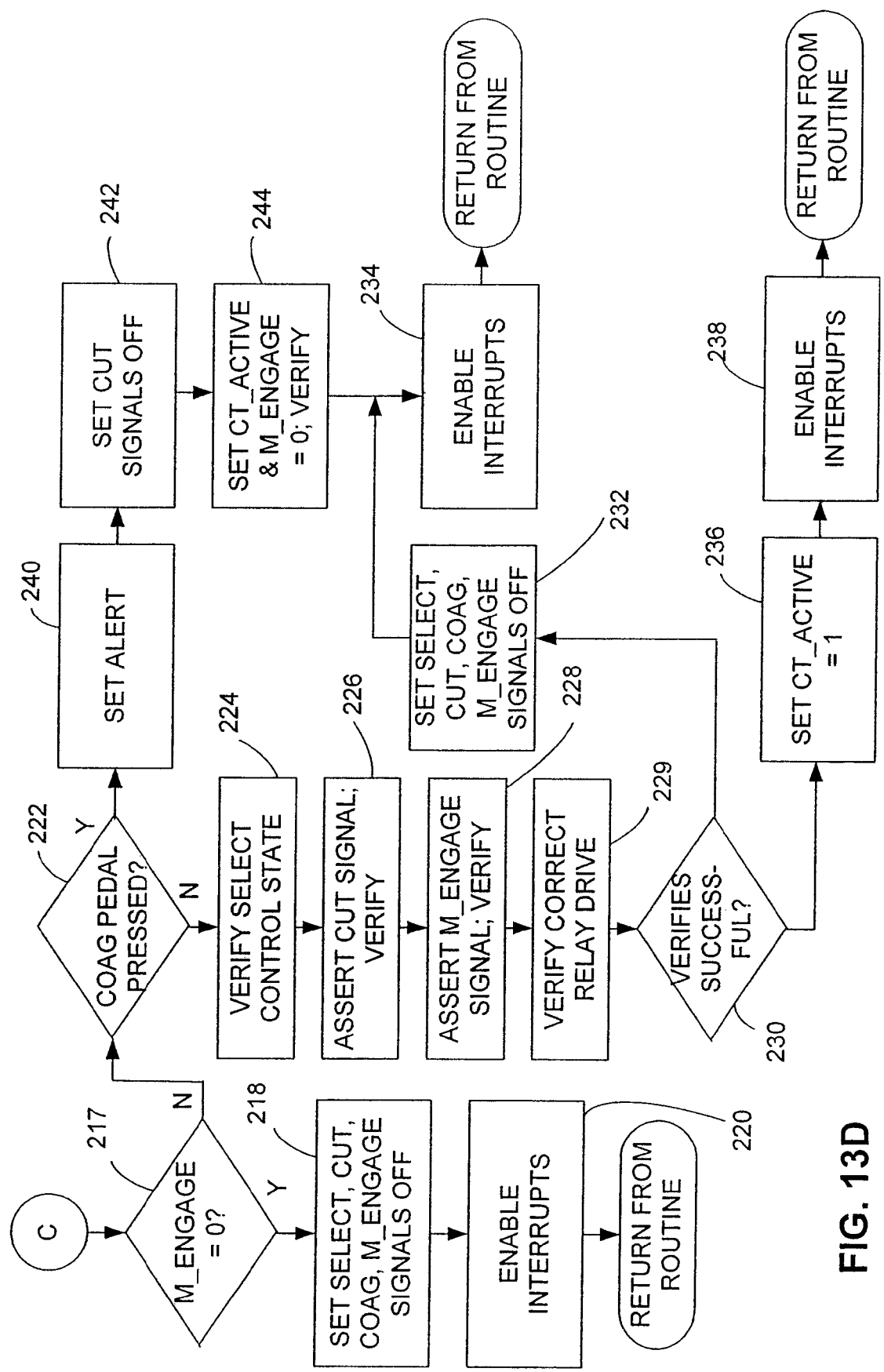
FIG. 13D is a continuation of the flow diagram of FIGS. 13A-C.
Figure 13E:
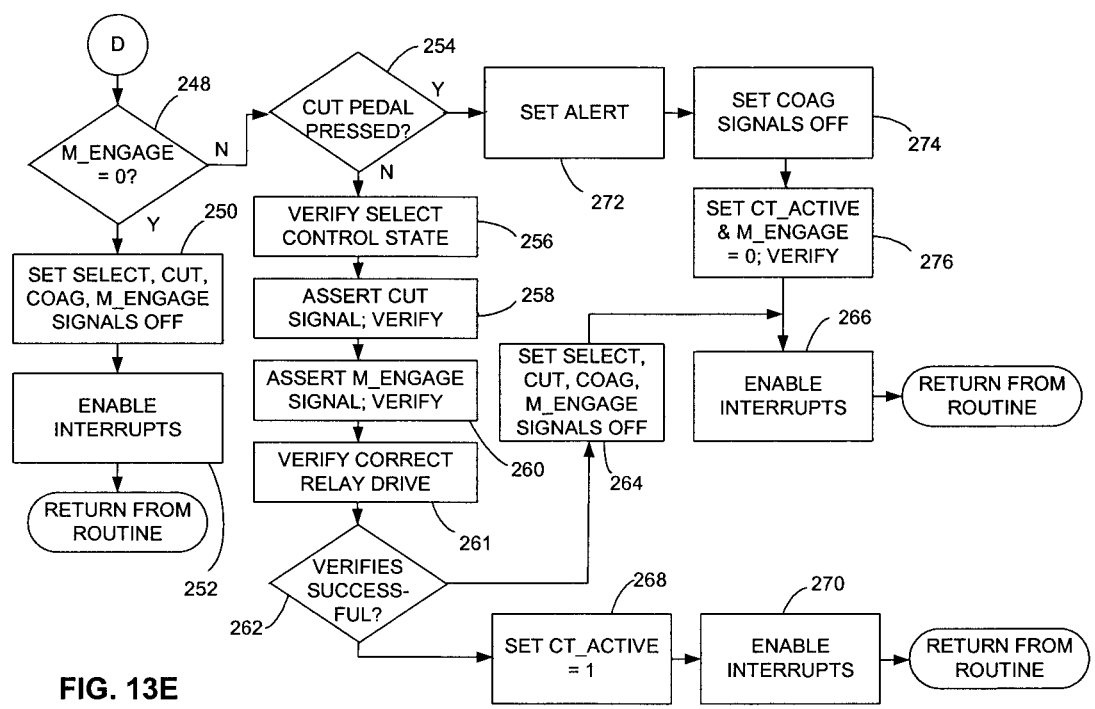
FIG. 13E is a continuation of the flow diagram of FIGS. 13A-D.

As illustrated in FIGS. 9-11, central controller unit 12 (FIG. 1) can cause information useful to the surgeon or other user to be displayed on display 18 (FIG. 1). The screen shown in FIG. 9 includes a graphical representation 130 of a foot control along with alphanumeric labels "CUT" and "COAG" that indicate, respectively, the left foot pedal is associated with a cutting function, and the right foot pedal is associated with a coagulation function. By viewing such a screen on display 18, the surgeon can quickly and easily ascertain the functions of each pedal without looking away from the surgical field. Note that embodiments of the invention in which the device user control is something other than a foot control, the screen can depict it and its device user inputs, however they may appear. Also note that central controller unit 12 applies the labels to the pedals or other representations of device user inputs in response to the functions of the electrosurgical device that is at that time actually plugged in and selected for use by the surgeon. That is, central control unit 12 applies dynamic labels corresponding to the functions it ascertained by reading the information from the intelligent adapter associated with the selected device.

The screen shown in FIG. 9 further includes an alphanumeric label or indication 132 that the selected electrosurgical device is "UNIPOLAR." The screen also includes some indications 134 that the devices that have been plugged in ("DEVICES AVAILABLE") are a "BIPOLAR" device on the first channel ("CH1"), a "HARMONIC" device on the third channel ("CH3") and a "UNIPOLAR" device on the fourth channel. The absence of an indication adjacent the label "CH2" indicates that no device has been plugged into the second channel. Another indication shows that the "DEVICE SELECTED" is of "TYPE: UNIPOLAR," is produced by "MAUFACTURER: VALLEYLAB" and is ValleyLab's "MODEL: ABC123-X." Still another indication shows the "SYSTEM STATUS" as "READY," indicating that the system is operational and the surgeon can use the selected device.

The screen shown in FIG. 10 is similar to that in FIG. 9 and illustrates that, as described above, the displayed information changes as the surgeon selects a different device. The graphical representation 136 indicates that the surgeon has selected a device having, as indicated by the alphanumeric labels, a left foot pedal associated with a "POWER LEVEL" function and a right foot pedal associated with a power "ON/OFF" function. Indication 138 indicates that the selected electrosurgical device is a "BIPOLAR" type. Similarly to FIG. 9, the screen also includes indications 140 that the devices that have been plugged in ("DEVICES AVAILABLE") are a "BIPOLAR" device on the first channel ("CH1"), a "HARMONIC" device on the third channel ("CH3") and a "UNIPOLAR" device on the fourth channel. As in FIG. 9, the absence of an indication adjacent the label "CH2" indicates that no device has been plugged into the second channel. Another indication shows that the "DEVICE SELECTED" is of "TYPE: BIPOLAR," is produced by "MAUFACTURER: OLYMPUS" and is Olympus's "MODEL: ABC123-X." As in FIG. 9, another indication shows the "SYSTEM STATUS" as "READY." The display may also include at least one verification status indicator and at least one verification command button. In this embodiment, the processor system is programmed or adapted to display an indication of the device verification status of the selected electrosurgical device.

In an embodiment of the invention, the control unit engages a smoke evacuation system upon activation of an electrosurgical device when the function is a surgical function. The smoke evacuation system may remain activated for a predetermined period of time. In an embodiment of the invention the smoke evacuation system comprises a smoke evacuator and an insufflator. As used herein, "surgical function" refers to a cutting or coagulation function of the electrosurgical device. As illustrated in FIG. 10, a bipolar device may have a power level function as well as a surgical function. The control system differentiates between the surgical and non-surgical functions and will activate the smoke evacuation system when the surgeon selects the surgical function. If the surgeon selects the power level function, the control system will not activate the smoke evacuation system. The control system may activate the smoke evacuation system by switch control electrical system or by remote computer command.

The screen shown in FIG. 11 is similar to those in FIGS. 9 and 10 and illustrates that status information can be displayed. For example, the screen includes a "SYSTEM ERROR" indication, indicating "NO FOOT CONTROL CONNECTED." As described in further detail below, central controller unit 12 senses when foot control 16 is connected, and if not connected, can display this indication in place of a graphical representation of a foot control to alert the user. Other indications 142 are similar to those described above with regard to FIGS. 9 and 10.

Note that any other status information or other information potentially of interest to a user can be displayed in addition to or alternatively to the information described above, such as an indication that a malfunction or error has occurred (e.g., a failed self-test).

In an embodiment of the invention the processor system is programmed or adapted to record surgical activity, thereby creating recorded information. In an embodiment of the invention, the processor system stores said recorded information.

Central controller unit 12 operates under the control of microcontroller 24, which is programmed to effect the method steps illustrated in FIGS. 12 and 13A-E. It should be noted that the illustrated programming relates to an exemplary embodiment of the invention in which the central user control has a left foot pedal and a right foot pedal as inputs. Nevertheless, persons skilled in the art to which the invention relates will readily be capable of providing programming in other embodiments, in which the central user control is of a type other than a foot control 16 with two such pedals. Also note that in FIGS. 13A-E, the term "CUT" (e.g., "CUT PEDAL," "CUT SIGNAL," etc.) is used to refer to the left pedal, and the term "COAG" (e.g., "COAG PEDAL," "COAG SIGNAL," etc.) is used to refer to the right pedal. This is done to facilitate understanding by persons skilled in the art, as a large number of conventional electrosurgical devices have a device user control comprising two pedals, in which the function of the two pedals can vary.

When a user first turns on the power, microcontroller 24 performs some initializations and a self-test at step 144. The self-test can include any suitable tests of the type commonly performed to verify proper operation of a microprocessor-based system, such as a CRC check of read-only program memory. If errors are detected at step 146, an error routine is performed at step 148. Although not illustrated in further detail, the error routine can include displaying error indications on display 18 and any other suitable measures such as disabling operation of any connected electrosurgical devices. At step 150, a main control loop routine is entered periodically (e.g., every 6.67 ms in the exemplary embodiment) as a result of a real-time interrupt. As described below, if a user depresses or activates a pedal of foot control 16 at any time during execution of the main control loop, it causes microcontroller 24 to receive a real-time interrupt and act upon the pedal activation by causing a signal applied to the selected device to be adjusted accordingly.

In the main control loop, at step 152, microcontroller 24 checks or senses whether any electrosurgical device has been connected, i.e., plugged in to one of channel connectors 36, 38, 40 and 42 (FIG. 2), since last performing this step. Microcontroller 24 does this by sensing a signal at channel connectors 36, 38, 40 and 42. When this signal is sensed, and if the electrosurgical device associated with that intelligent adapter is not already on-line, microcontroller 24 initiates serial transfer of data from the intelligent adapter memory 68 (FIG. 4) into its SPI subsystem port. If no errors were encountered during the transfer, microcontroller 24 causes the remote controller 14 and display 18 to display the indications described above (e.g., device type, manufacturer, model, etc.) that identify the electrosurgical device on that channel.

At step 154, microcontroller 24 similarly checks or senses at the SPI port whether any electrosurgical device has been disconnected since the step was last performed. If a device has been disconnected during that time, indications that had been displayed are removed or extinguished, or it is otherwise indicated to a user that a device is no longer present on that channel.

Similarly, at step 156, microcontroller 24 senses at its serial communication interface (SCI) subsystem port whether remote controller 14 has been connected, i.e., plugged in to connector 46 (FIG. 2) since the step was last performed. At step 158, microcontrollor 24 senses whether remote controller 14 has been disconnected.

At step 160, microcontroller 24 senses whether a user has pressed switch 56 (FIG. 2). Switch 56 can be a momentary-contact pushbutton or toggle switch that serves as a secondary means for selecting an electrosurgical device, the primary means being remote controller 14. Microcontroller 24 responds to each press of switch 56 by advancing to the next channel. That channel becomes the selected channel, and the previous channel is de-selected. Indications of the selection and de-selection are reflected accordingly in remote controller 14 and display 18.

At step 162, microcontroller processes any messages to be displayed on display 18 in response to the connection, disconnection, selection or de-selection of a device as described above with regard to the main control loop.

If microcontroller 24 receives an interrupt, at step 164, it initializes general software indicators, such as timers, counters and other variables, and determines at step 166 whether there has been a foot pedal activation by reading via I/O circuitry and PPIs 32 and 34 signals received from foot pedal connector 44. At step 168, it verifies that operations are "off," i.e., that control signals received from connectors 36, 38, 40 and 42 via I/O circuitry 30 and PPIs 32 and 34 have the expected values and are functioning properly, and returns from the interrupt to the main control loop. If the interrupt was caused by a foot pedal activation, at step 170, microcontroller 24 disables interrupts and, at step 172, performs a routine to process the foot pedal command received at the SPI port, as described in further detail below. Upon returning from the routine, at step 174, microcontroller re-enables interrupts and returns from the interrupt to the main control loop.

The above-mentioned step 172, in which a foot control activation is processed, is illustrated in further detail in FIGS. 13A-E. At step 176, it is determined whether a cutting operation is already in progress. Microcontroller 24 can do this by checking whether a flag or other indicator indicates a state in which a foot pedal associated with a cutting function has already been depressed or activated. If a cutting operation is not already in progress, then at step 178 it is determined whether a coagulation function is already in progress, i.e., the process is in a state in which a foot pedal associated with a coagulation function has already been depressed or activated. If a coagulation function is not already in progress, then at step 180 it is determined whether any system errors are present. Although not specifically described for purposes of clarity, some of the "verify" steps described below with regard to FIGS. 13B-E can include self-tests such as checking RAM 26 and internal memory of microcontroller 24 and checking for proper operation of foot control 16. If any such test indicates an error condition, a flag or indicator is set. Step 180 checks that indicator. If there are system errors, then at step 182 microcontroller 24 causes all signals to the electrosurgical device to be in an "off" state, and returns from the foot control activation processing routine (i.e., returns from step 172).

If at step 180 no system errors were detected, then at step 184 it is determined whether a foot pedal associated with a cutting function has been depressed. If a foot pedal associated with a cutting function has not been depressed, then at step 186 it is determined whether a foot pedal associated with a coagulation function has been pressed. If neither foot pedal has been pressed, microcontroller 24 returns from the foot control activation processing routine.

If at step 176 it is determined that a cutting operation is already in progress, then at step 187 microcontroller 24 verifies that the foot pedal associated with the coagulation function has not been pressed, because such a state could represent a foot control circuit failure or at least an ambiguous condition. If the foot pedal associated with the coagulation function has not been pressed, microcontroller 24 determines at step 188 whether any system errors are present (as described above with regard to step 180). If there are system errors, then at step 190 microcontroller 24 causes all signals to the electrosurgical device relating to the cutting function to be in an "off" or de-energized state, verifies that the signals are off, and returns from the foot control activation processing routine. If there are no system errors, then at step 192 it is determined whether the foot pedal associated with the cutting function is still depressed. If it is not still depressed, then at step 194 microcontroller 24 causes all signals to the electrosurgical device relating to the cutting function to be in an "off" state, sets a master engage signal ("M_ENGAGE") that enables operation of the system as a whole to "off" or "0", and returns from the foot control activation processing routine. If that foot pedal is still depressed, then at step 196 microcontroller 24 performs some verifications. These can include: verifying that the master engage signal is asserted (e.g., is "on" or "1"); verifying that a foot command has been detected; verifying that a device that the software indicates is (logically) selected is actually (electrically) selected; verifying that the signals from foot control 16. At step 198, microcontroller 24 determines whether the verifies were successful. If the verifies were successful, microcontroller 24 returns from the foot control activation processing routine. If the verifies were not successful, then at step 200 microcontroller 24 notes that result by setting some system error variables and continues at step 194 as described above.

If at step 178 it is determined that a coagulation operation is already in progress, then at step 201 microcontroller 24 verifies that the foot pedal associated with the cutting function has not been pressed, because such a state could represent a foot control circuit failure or at least an ambiguous condition. If the foot pedal associated with the cutting function has not been pressed, then at step 202 microcontroller 24 determines whether any system errors are present (as described above with regard to steps 180 and 188). If there are system errors, then at step 204 microcontroller 24 causes all signals to the electrosurgical device relating to the cutting function to be in an "off" state, and returns from the foot control activation processing routine. If there are no system errors, then at step 206 it is determined whether the foot pedal associated with the cutting function is still depressed. If it is not still depressed, then at step 208 microcontroller 24 causes all signals to the electrosurgical device relating to the coagulation function to be in an "off" state, sets the master engage signal to "off" or "0", and returns from the foot control activation processing routine. If that foot pedal is still depressed, then at step 210 microcontroller 24 performs the same verifications as described above with regard to step 196. At step 212, microcontroller 24 determines whether the verifies were successful. If the verifies were successful, microcontroller 24 returns from the foot control activation processing routine. If the verifies were not successful, then at step 214 microcontroller 24 notes that result by setting some system error variables and continues at step 208 as described above.

If at step 184 it is determined that the pedal associated with the cutting function has been depressed, microcontroller 24 disables all interrupts at step 216 and determines at step 217 if the status of the master engage signal is "off" or "0". If at step 217 it is determined that the master engage signal is off, then at step 218 microcontroller 24 causes all signals to the electrosurgical device relating to the cutting and coagulation functions as well as the master engage signal to be in an "off" state, re-enables the interrupts at step 220, and returns from the foot control activation processing routine. If, however, at step 217 it is determined that the master engage signal is on, then at step 222 it is determined whether the pedal associated with the coagulation function is "off," i.e., not depressed. If the pedal is not depressed, then at step 224 the select signal state is verified. At step 226, the signal to the device that causes the device to perform the cutting function is asserted or changed to an "on" or "1" state and verified. At step 228, the master engage signal is asserted or changed to an "on" or "1" state and verified.

At step 230, microcontroller 24 determines whether the verifies were successful. If the verifies were successful, microcontroller 24 returns from the foot control activation processing routine. If any of the verifies was not successful, then at step 232 microcontroller 24 disables all signals to the device associated with the cutting and coagulation function as well as the master engage signal and sets system error variables before re-enabling interrupts at step 234 and returning from the foot control activation processing routine. If, however, all verifies were successful, then microcontroller notes that cutting is the active state by setting appropriate variables or flags at step 236, re-enables interrupts at step 238, and returns from the foot control activation processing routine.

If at step 222 it is determined that the pedal associated with the coagulation function is depressed, i.e., not "off," then at step 240 microcontroller 24 sets an alert indicator that indicates both pedals (cut and coagulation) are "on" or depressed. At step 242 microcontroller 24 then sets all signals to the device that are associated with the cutting function to an "off" state and, at step 244, notes the change in status by setting appropriate variables or flags before continuing with step 234, where it re-enables interrupts before returning from the foot control activation processing routine.

If at step 186 it is determined that the pedal associated with the cutting function has been depressed, microcontroller 24 disables all interrupts at step 246 and determines at step 248 if the status of the master engage signal is "off" or "0". If at step 248 it is determined that the master engage signal is off, then at step 218 microcontroller 24 causes all signals to the electrosurgical device relating to the cutting and coagulation functions as well as the master engage signal to be in an "off" state, re-enables the interrupts at step 220, and returns from the foot control activation processing routine. If, however, at step 248 it is determined that the master engage signal is "on"

or "1", then at step 254 it is determined whether the pedal associated with the cutting function is "off," i.e., not depressed. If the pedal is not depressed, then at step 256 the select signal control state is verified. At step 258, the signal to the device that causes the device to perform the cutting function is asserted or changed to an "on" or "1" state and verified. At step 260, the master engage signal is asserted or changed to an "on" or "1" state and verified.

At step 262, microcontroller 24 determines whether the verifies were successful. If the verifies were successful, microcontroller 24 returns from the foot control activation processing routine. If any of the verifies was not successful, then at step 264 microcontroller 24 disables all signals to the device associated with the cutting and coagulation functions as well as the master engage signal, and sets system error variables before re-enabling interrupts at step 266 and returning from the foot control activation processing routine. If, however, all verifies were successful, then microcontroller 24 notes that cutting is the active state by setting appropriate variables or flags at step 268, re-enables interrupts at step 270, and returns from the foot control activation processing routine.

If at step 254 it is determined that the pedal associated with the coagulation function is depressed, i.e., not "off," then at step 272 microcontroller 24 sets an alert indicator that indicates both pedals (cut and coagulation) are "on" or depressed. At step 274 microcontroller 24 then sets all signals to the device that are associated with the cutting function to an "off" state and, at step 276, notes the change in status by setting appropriate variables or flags before continuing with step 266, where it re-enables interrupts before returning from the foot control activation processing routine.

As persons skilled in the art to which the invention relates understand, the above-described method steps and the software embodying them can be structured and can flow in various ways other than the exemplary structure and flow described above. The software can be modularized or otherwise structured in any suitable manner, with the above-mentioned "routines" and use of interrupts being only one example.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A control system for a plurality of independent electrosurgical devices, wherein the plurality of electrosurgical devices comprise at least one first said electrosurgical device having a first output function or operating characteristic and at least a second said electrosurgical device having a second output function or operating characteristic that differs from the first output function or operating characteristic, each said electrosurgical device controllable by a respective associated device user control, the control system comprising:

a central user control operable by a user to control any of the plurality of electrosurgical devices;

a device selector operable by a user to select one of the electrosurgical devices for control;

a plurality of intelligent adapters, each associated with one of the electrosurgical devices and programmed or adapted to communicate information relating to the associated electrosurgical device; and a processor system responsive to operation of the central user control, each said intelligent adapter removably connectable to the processor system, the processor system programmed or adapted to respond to operation of the central user control by controlling the selected electrosurgical device in accordance with information communicated by the associated intelligent adapter, wherein the central user control is configured to control at least one of said first electrosurgical device having the first output function or operating characteristic and the second electrosurgical device having the second output function or characteristic;

wherein the communicated information characterizes operation of the device user control associated with the selected electrosurgical device;

wherein the device selector is disposed separately and remotely from the processor system; and wherein the device selector is housed in an enclosure in communication with the processor system, the device selector including a disposable anti-static sheath on the enclosure.

2. The control system claimed in claim 1, wherein: the central user control includes a plurality of central user inputs operable by a user to control functions of the electrosurgical devices, wherein each function of an electrosurgical device is associated with one of a plurality of device user inputs of the associated device user control; and the device selector is operable by a user to selectably associate each central user input with one of the functions of a selected electrosurgical device.

3. The control system claimed in claim 2, wherein: the plurality of central user inputs comprises a left foot pedal and a right foot pedal; the device selector is operable by a user to simultaneously associate the left foot pedal with one of the functions of the first electrosurgical device and associate the right foot pedal with one of the functions of the second electrosurgical device.

4. The control system claimed in claim 3, wherein the functions include a cut function and a coagulate function.

5. The control system claimed in claim 1, wherein each said intelligent adapter includes a cable with a first connector removably connectable to the device user control of the associated electrosurgical device and a second connector removably connectable to an enclosure that contains the processor system.

6. The control system claimed in claim 5, wherein each said intelligent adapter includes a module integral with the cable that contains a processor and memory.

7. The control system claimed in claim 1, further comprising a display, wherein the processor system is programmed or adapted to display information communicated by the associated intelligent adapter.

8. The control system claimed in claim 7, wherein information communicated by the associated intelligent adapter is displayed superimposed upon laparoscopic video imagery.

9. The control system claimed in claim 7, wherein the display is housed separately and remotely from the processor system.

10. The control system claimed in claim 7, wherein: the communicated information identifies a device type of the selected electrosurgical device; and the processor system is programmed or adapted to display an indication of the device type of the selected electrosurgical device.

11. The control system claimed in claim 7, wherein: the communicated information identifies a manufacturer and model of the selected electrosurgical device; and the processor system is programmed or adapted to display indications of the manufacturer and model of the selected electrosurgical device.

12. The control system claimed in claim 7, wherein: the communicated information identifies a function of the selected electrosurgical device; and the processor system is programmed or adapted to display an indication of the function of the selected electrosurgical device.

13. A control system for a plurality of independent electrosurgical devices, wherein the plurality of electrosurgical devices comprise at least one first said electrosurgical device having a first output function or operating characteristic and at least a second said electrosurgical device having a second output function or operating characteristic that differs from the first output function or operating characteristic, each said electrosurgical device controllable by a respective associated device user control, the control system comprising:
   a central user control operable by a user to control any of the plurality of electrosurgical devices;
   a device selector operable by a user to select one of the electrosurgical devices for control;
   a plurality of intelligent adapters, each associated with one of the electrosurgical devices and programmed or adapted to communicate information relating to the associated electrosurgical device; and
   a processor system responsive to operation of the central user control, each said intelligent adapter removably connectable to the processor system, the processor system programmed or adapted to respond to operation of the central user control by controlling the selected electrosurgical device in accordance with information communicated by the associated intelligent adapter, wherein the central user control is configured to control at least one of said first electrosurgical device having the first output function or operating characteristic and the second electrosurgical device having the second output function or characteristic;
   wherein the communicated information characterizes operation of the device user control associated with the selected electrosurgical device; and
   wherein the device user control associated with each said electrosurgical device of the plurality of electrosurgical devices comprises a foot control; and the central user control comprises a foot control.

14. The control system claimed in claim 13, wherein the device selector is included in an electrosurgical device.

15. The control system claimed in claim 13, wherein: the device user control associated with each said electrosurgical device comprises two foot pedals; and the central user control includes two foot pedals.

16. A control system for a plurality of independent electrosurgical devices, each controllable by an associated device user control, comprising:
   a central user control operable by a user to control any of the electrosurgical devices;
   a device selector operable by a user to select one of the electrosurgical devices;
   a plurality of intelligent adapters, each associated with one of the electrosurgical devices and programmed or adapted to communicate information relating to the associated electrosurgical device; and
   a processor system responsive to operation of the central user control, each intelligent adapter removably connectable to the processor system, the processor system programmed or adapted to respond to operation of the central user control by controlling the selected electrosurgical device in accordance with information communicated by the associated intelligent adapter;
   wherein the communicated information characterizes operation of the device user control associated with the selected electrosurgical device, wherein each of the plurality of independent electrosurgical devices comprises a device control unit connected to an electrosurgical instrument, and wherein the intelligent adapters are each connected to a respective said device control unit for communicating control signals from the central user control to the selected electrosurgical device; and
   wherein the device user control associated with each said electrosurgical device of the plurality of electrosurgical devices comprises a foot control; and the central user control comprises a foot control.

17. The control system of claim 16 wherein power is not provided to the electrosurgical devices through the intelligent adapters.

18. A control system for a plurality of independent electrosurgical devices, each said electrosurgical device including a device control unit and an associated device user control, said control system comprising:
   a central user control operable by a user to control any of the electrosurgical devices;
   a device selector operable by a user to select one of the electrosurgical devices;
   a plurality of intelligent adapters, each connected to one of the device control units of a corresponding one of the electrosurgical devices, the intelligent adapters programmed or adapted to communicate information relating to the associated electrosurgical device; and
   a processor system responsive to operation of the device selector and the central user control, each said intelligent adapter removably connectable to the processor system, the processor system programmed or adapted to receive the information related to the associated electrosurgical device from the associated intelligent adapter, the processor system programmed or adapted to respond to operation of the device selector to determine the electrosurgical device to be controlled, and the processor system programmed or adapted to respond to operation of the central user control by providing control signals to the device control unit of the selected electrosurgical device with the associated intelligent adapter in accordance with the information communicated by the associated intelligent adapter;
   wherein the communicated information characterizes operation of the device user control associated with the selected electrosurgical device; and
   wherein the device user control associated with each said electrosurgical device of the plurality of electrosurgical devices comprises a foot control; and the central user control comprises a foot control.

19. The control system according to claim 18, wherein power is not provided to the electrosurgical devices through the intelligent adapters.

20. An electrosurgical system comprising:
   a plurality of independent electrosurgical devices, a first one of the electrosurgical devices having a first output function or operating characteristic and a second one of the electrosurgical devices having a second output function or operating characteristic that differs from the first output function or operating characteristic;
   a device user control for each of the electrosurgical devices;
   a central user control operable by a user to control any of the plurality of independent electrosurgical devices;

a device selector operable by a user to select one of the electrosurgical devices for control;

a plurality of intelligent adapters, each associated with one of the electrosurgical devices and programmed or adapted to communicate information relating to the electrosurgical devices; and a housing having a processor system therein, the processor system being responsive to operation of the central user control, with the intelligent adapters connecting the electrosurgical devices to the housing and being removably connectable to the housing for communicating with the processor system, the processor system programmed or adapted to respond to operation of the central user control by controlling a selected one of the electrosurgical devices in accordance with information communicated by an associated one of the intelligent adapters, wherein the central user control is configured to control at least one of the first one of the electrosurgical devices having the first output function or operating characteristic and the second one of the electrosurgical devices having the second output function or operating characteristic;

wherein power for powering the first output function or operating characteristic of the first one of the electrosurgical devices and for powering the second output function or operating characteristic of the second one of the electrosurgical devices does not pass from the housing to the electrosurgical devices; and wherein the device user control associated with each said electrosurgical device of the plurality of electrosurgical devices comprises a foot control; and the central user control comprises a foot control.

* * * * *